United States Patent [19]
Ramachandran et al.

[11] Patent Number: 5,344,766
[45] Date of Patent: Sep. 6, 1994

[54] PROCESS FOR THE PRODUCTION OF BIOPROTEINS

[75] Inventors: Ramakrishnam Ramachandran, Allendale; Arthur I. Shirley, Piscataway, both of N.J.

[73] Assignee: The BOC Group, Inc., New Providence, N.J.

[21] Appl. No.: 37,943

[22] Filed: Mar. 26, 1993

[51] Int. Cl.$^5$ .......................... C12P 21/04; C07K 3/00
[52] U.S. Cl. .................. 435/71.2; 435/71.1; 530/350; 530/427
[58] Field of Search ............... 530/427, 350; 435/71.1, 435/71.2, 167

[56] References Cited

U.S. PATENT DOCUMENTS

| | | | |
|---|---|---|---|
| 3,816,250 | 6/1974 | Overbeck et al. | 435/71.2 |
| 3,833,477 | 9/1974 | Brugerolle et al. | 435/243 |
| 4,690,696 | 9/1987 | Sircar et al. | 55/26 |

OTHER PUBLICATIONS

Harrison, "Making Protein from Methane", *Chemtechm* Sep. 1976, pp. 570–574.
Klass et al., "Key Process Factors in the Microbial Conversion of Methane to protein," Chemical Eng. Prog. Symp. Series, No. 93 vol. 65, 1969, pp. 72–79.
"A Fairytale in Odense", Statoil Magazine, Issue 90 2, pp. 12–15.

*Primary Examiner*—Herbert J. Lilling
*Attorney, Agent, or Firm*—Coleman R. Reap; Larry R. Cassett

[57] ABSTRACT

Proteins are prepared by the reaction of a hydrocarbon utilizing microbe on a low molecular weight hydrocarbon, such as methane, in an aqueous medium in the presence of oxygen and a fixable nitrogen compound in a recycle process in which unreacted hydrocarbon and oxygen are recycled to the protein manufacturing reactor. Sufficient hydrocarbon is introduced into the system to prevent the formation of a flammable mixture therein. Part or all of the hydrocarbon can be introduced into the system downstream of the protein reactor, where the propensity of forming a flammable gas mixture is greatest.

18 Claims, 3 Drawing Sheets

PROCESS FOR THE PRODUCTION OF BIOPROTEINS

BACKGROUND OF THE INVENTION

This invention relates to the production of proteins, and more particularly to a recycle process for the manufacture of proteins by the biochemical oxidation of gaseous hydrocarbons in the presence of a nitrogenous nutrient.

Proteins can be produced by the microbial conversion of hydrocarbons under fermentation conditions. In conducting such conversions a hydrocarbon is contacted in an aqueous medium containing a nitrogen source and other desired nutrients with an oxygen-containing gas. The protein produced in the reaction remains in the aqueous medium and unused oxygen and byproduct carbon dioxide are removed from the reaction as a gas phase. More recently, it has been discovered that greater protein yields are realized when the conversion is carried out using an enriched oxygen-containing gas; accordingly, later hydrocarbon conversion processes are conducted using oxygen-enriched air or high purity oxygen as the oxygen-containing gas.

Since the reaction occurs in the aqueous phase and the solubility of oxygen in water is relatively low, it is desirable to use excess oxygen-containing gas to effect reasonable conversion rates. When an oxygen-enriched gas or substantially pure oxygen is used as the oxygen source it is important for economic reasons to recover unused oxygen-enriched gas. Brugerolle et al. U.S. Pat. No. 3,833,477, discloses the separation of oxygen from water vapor and carbon dioxide contained in a gaseous effluent stream from an aerobic fermentor by cooling the gaseous effluent and condensing water vapor and carbon dioxide from the gaseous effluent. The separated oxygen can then be recycled to the fermentor. Sicar et al. U.S. Pat. No. 4,690,696 discloses the separation by pressure swing adsorption of oxygen from carbon dioxide in an organic substance fermentor effluent gas stream, and recycle of the recovered oxygen to the fermentor.

Harrison, "Making Protein from Methane", Chemtech, September, 1976, pp 570–574, and Klass et al., "Key Process Factors in the Microbial Conversion of Methane to Protein", Chemical Engineering Progress Symposium Series, No. 93, Vol. 65 (1969), pp 72–79 describe the metabolism of methane to protein concentrate by means of a methane utilizing microbe. There is no discussion of recovery of unused oxygen or methane in either of these articles. A continuous reaction process for converting methane to protein by the reaction of methane with oxygen and nutrients in the presence of methane-utilizing bacteria is disclosed in an article entitled "A Fairytale in Odense", appearing in Statoil Magazine, issue 90 2, pp 12–15.

More efficient and economical protein manufacturing processes are continuously sought. The efficiency and economics of hydrocarbon oxidation protein production processes could be considerably enhanced if both the excess oxygen and excess hydrocarbon from a gaseous hydrocarbon protein production plant could be safely recovered and recycled. The present process provides such an improvement.

SUMMARY OF THE INVENTION

According to the process of the invention protein is produced by oxidizing a gaseous hydrocarbon with an oxygen-enriched gas stream, such as oxygen-enriched air or substantially pure oxygen, in a reaction zone containing an aqueous medium, various nutrients and a hydrocarbon utilizing microbe, thereby producing protein as the principal product and carbon dioxide as byproduct; recovering the protein product from the reaction zone; removing a nonflammable gaseous stream containing carbon dioxide byproduct and excess gaseous hydrocarbon and oxygen from the reaction zone; separating hydrocarbon and oxygen from carbon dioxide and other components of the gaseous effluent, e.g. nitrogen and/or argon, in a manner such that the creation of a flammable mixture of hydrocarbon and oxygen is avoided, and recycling the separated hydrocarbon and oxygen to the reaction zone. The creation of a flammable gas mixture is avoided by ensuring that the concentration of oxygen in all parts of the system is sufficiently low that the separated gas streams are nonflammable. This is accomplished by either introducing a sufficient excess of hydrocarbon into the reactor to render all separated gas streams nonflammable or by introducing all or a part of the gaseous hydrocarbon from the feed and/or recycle streams feed to the system downstream of the protein manufacturing reactor.

DESCRIPTION OF THE PREFERRED EMBODIMENTS

Figure 1:
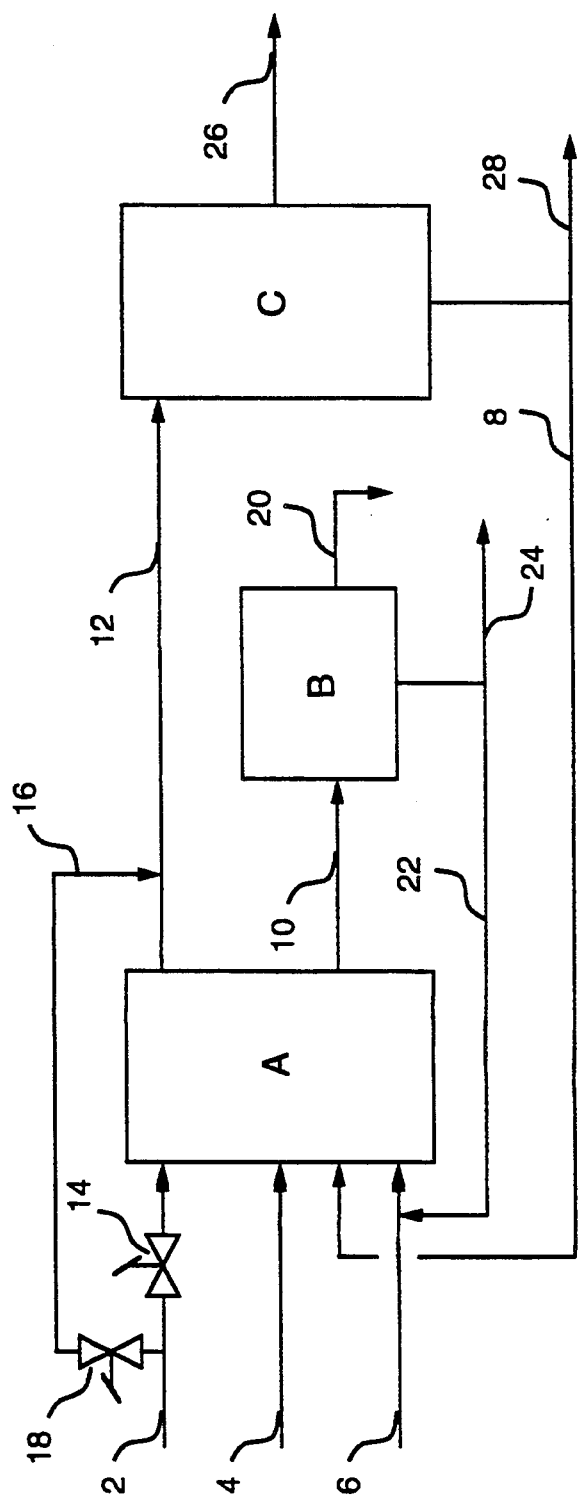
FIG. 1 illustrates in a block diagram one embodiment of a system for producing proteins in accordance with the process of this invention.

The hydrocarbon component used as feed in the process of the invention may be any saturated or ethylenically unsaturated hydrocarbon or mixture of saturated and/or ethylenically unsaturated hydrocarbons having 1 to 5 carbon atoms. Included in this category are saturated straight- and branch-chained alkanes, such as methane, ethane, propane, n-butane, i-butane, n-pentane, etc., and ethylenically unsaturated straight- and branch-chained alkenes, such as ethene, propene, n-butene, i-butene, n-pentene, etc. The preferred hydrocarbons are the saturated hydrocarbons having 1 to 4 carbon atoms, i.e. methane, ethane, propane and the butanes, and the ethylenically unsaturated hydrocarbons having 2 to 4 carbons, i.e. ethane, propene and the butenes. The hydrocarbon component may be in the form of natural gas, which is predominantly methane with small amounts of other low molecular weight hydrocarbons and inert gases, such as nitrogen. The most preferred hydrocarbon source is natural gas and the most preferred hydrocarbon is methane.

The oxygen-rich gas used in the invention may be substantially pure oxygen or an oxygen-inert gas mixture in which the oxygen concentration is at least 60 volume percent. An "inert gas" is any gas that will not chemically react with any component of the protein-producing reaction mixture or reaction product, or otherwise interfere with the production of the desired protein product. Typical oxygen-inert gas mixtures that can be used in the process of the invention include oxygen-enriched air, oxygen-nitrogen mixtures and oxygen-argon mixtures. In preferred embodiments of the invention the oxygen concentration of the oxygen-rich gas is at least 90 volume percent. Substantially pure oxygen is most preferred because the introduction of gaseous components other than reactant gases is avoided. This is advantageous since the final pressure swing step can be designed to reject only carbon dioxide.

The source of fixable nitrogen for the protein synthesis is not critical and, in general, any nitrogen source used with microbes and hydrocarbons to produce proteins can be used in the invention. The specific fixable nitrogen source used will depend on several system variables, such as the particular hydrocarbon and microbe used, the culture pH, the desired product amino acid distribution, etc. Typical fixable nitrogen sources include anhydrous ammonia, ammonium hydroxide, inorganic ammonium salts and organic ammonium compounds.

Similarly, the source of supply of other elements and nutrients, such as phosphorus, sulfur and other minerals can be any of the many compounds used in protein syntheses. Typical phosphate sources include, for example, ammonium phosphate and phosphoric acid. Minerals such as calcium, iron, magnesium, manganese, potassium and sodium, can be supplied, for example, as sulfates or hydroxides.

The hydrocarbon-utilizing microbe used in the process of the invention can be any organism that produces edible proteins from hydrocarbons. The preferred organisms are the methanotropic bacteria. The particular organism used in the process of the invention forms no part of the invention.

According to one embodiment of the process of the invention, the gaseous hydrocarbon component and oxygen source contact the nutrients and the hydrocarbon utilizing microbe in an aqueous reaction medium contained in a reaction vessel. Gaseous components removed from the reaction vessel are next introduced into a carbon dioxide separator which is preferably an adsorption vessel containing an adsorbent which more strongly adsorbs carbon dioxide than oxygen and the hydrocarbon component(s). The oxygen and hydrocarbon(s) together pass through the carbon dioxide separator, and these are recycled to the reaction vessel. The carbon dioxide is removed from the separator and disposed of in a suitable manner. In this embodiment, the concentration of oxygen in the gaseous effluent is maintained below the threshold level for flammable gas mixtures by maintaining the hydrocarbon concentration introduced into the system at a concentration sufficiently high that it, in combination with the carbon dioxide produced during the protein synthesis reaction, prevents the formation of a flammable mixture anywhere in the system.

In a second embodiment, the gaseous effluent from the reaction vessel first enters an adsorption vessel which contains an adsorbent which more strongly adsorbs hydrocarbon component(s) than carbon dioxide and oxygen. The hydrocarbon component is desorbed from the adsorbent and is recycled to the reactor. The oxygen-carbon dioxide mixture passes through the adsorption vessel as nonadsorbed gas and is introduced into a second gas separation vessel. The second separation vessel may be any device which effects the separation of carbon dioxide and oxygen, such as an adsorption unit, an absorption unit or a membrane separator. It is preferably an adsorption vessel containing an adsorbent which more strongly adsorbs carbon dioxide than oxygen. The oxygen passes through the second adsorption vessel as nonadsorbed gas, and it is recycled to the reaction vessel. In this embodiment, the high concentration of hydrocarbon and carbon dioxide in the effluent from the reactor prevents the formation of a flammable mixture in the line between the reactor and the first adsorption vessel, the high concentration of hydrocarbon in the hydrocarbon recycle line prevents the formation of a flammable gas mixture in this line, and the low concentration of hydrocarbon in the line between the first and second adsorption vessels and in the oxygen recycle line from the second adsorption vessel prevents the formation of a flammable gas mixture in these lines.

In a third embodiment, the gaseous effluent from the reaction vessel first enters an adsorption vessel which contains an adsorbent which more strongly adsorbs hydrocarbon component(s) and carbon dioxide than oxygen. The oxygen passes through the adsorption vessel as nonadsorbed gas and is recycled to the reactor. The hydrocarbon-carbon dioxide adsorbed phase is then desorbed from the first adsorption vessel and introduced into a carbon dioxide separator. The carbon dioxide separator may be any device which effects the separation of carbon dioxide and hydrocarbons, such as an adsorption unit or an absorption unit. It is preferably an adsorption vessel containing an adsorbent which more strongly adsorbs carbon dioxide than hydrocarbons or an adsorbent which more strongly adsorbs hydrocarbons than carbon dioxide. The hydrocarbon is recovered from the second separator and recycled to the reaction vessel. In this embodiment, the high concentration of hydrocarbon and carbon dioxide in the effluent from the reactor prevent the formation of a flammable mixture in the line between the reactor and the first adsorption vessel, the low concentration of hydrocarbon in the oxygen recycle line prevents the formation of a flammable gas mixture in this line, and the high concentration of hydrocarbon in the line between the first and second adsorption vessels and in the hydrocarbon recycle line from the second separation vessel prevents the formation of a flammable gas mixture in these lines.

The hydrocarbon concentration in the reaction zone can be maintained at the desired level by controlling the rate of fresh hydrocarbon feed introduced into the system and the amount of hydrocarbon recycled from the recovery section. Fresh hydrocarbon can be introduced directly into the protein reaction vessel, or it can be introduced into the line carrying the gaseous effluent from the reaction vessel, or part of the fresh hydrocarbon can be fed directly into the reaction vessel and the remainder into the line carrying gaseous effluent from the reactor. With respect to the hydrocarbon recovered from the separators, all of it can be recycled to the reaction zone or part can be recycled and the remainder removed from the system by purging. As an alternative to recycling the hydrocarbon to the reaction zone, part or all of the hydrocarbon recycle stream from the separators can be introduced into the effluent from the reactor.

The invention can be better understood from the accompanying drawings. Auxiliary equipment, including compressors, heat exchangers and valves not necessary for an understanding of the invention, have been omitted from the drawings to simplify discussion of the invention.

Turning now to the drawings, the system of the invention illustrated in FIG. 1 includes a protein reactor, A, a protein recovery unit, B and a carbon dioxide separator, C.

Reactor A may be any appropriate vessel in which proteins are produced by the reaction of a hydrocarbon source and oxygen in an aqueous environment and from which the protein product and unreacted gaseous components are removable either on a batch basis or continuously. Suitable reaction vessels generally contain means for heating or cooling and agitating the reactor contents to ensure efficient contact between the reactants and the microbe. The reactor vessel may be of the batch type or continuous type. In a batch type reactor the aqueous medium, the fixable nitrogen compound, the microbe and any other solid nutrients that are to be used in the process are generally introduced into the reactor before the reaction commences, and the gaseous components are introduced continuously during the reaction period. Upon completion of batch type reactions the reactor contents are removed from the reactor and the protein product is recovered from the aqueous medium.

In continuous process operations, on the other hand, the aqueous medium containing the nutrients and the microbe is continuously passed through the reaction zone, as are the gaseous components. The protein product is continuously recovered from the aqueous medium by, for example, passing a small stream of the aqueous medium through a separating means such as a centrifuge to recover the protein, and returning the aqueous filtrate to the reactor. In such a system the gaseous effluent is continuously withdrawn from the vapor space at the top of the reactor. Such a system is illustrated and described the Statoil Magazine cited above. The invention is described in detail below as applied to continuous process operations and equipment.

Reactor A is provided on its inlet side with fresh hydrocarbon feed line 2, oxygen component feed line 4, aqueous medium feed line 6 and hydrocarbon and oxygen recycle line 8, and on its product discharge side with aqueous medium effluent line 10 and gaseous effluent line 12. Hydrocarbon feed line 2 is equipped with valve 14, and bypass line 16, fitted with valve 18 connects hydrocarbon feed line 2 with gaseous effluent line 12. Line 10 connects reactor A to protein recovery unit B and gaseous effluent line 12 connects reactor A to separator C.

Protein recovery unit B can be any suitable apparatus, such as filter means, that can be used to separate the protein product from the aqueous medium. Unit B is provided with protein product line 20 and aqueous medium recycle line 22. Line 22, which joins protein recovery unit B with aqueous medium feed line 6 is also provided with spent aqueous medium discharge line 24.

The principal purpose of separator C is to prevent carbon dioxide buildup in the system and this unit can be any device which will accomplish this result. Separator C is usually an adsorber, an absorber, a condenser or a membrane separation unit, and it may comprise a single separator or a train of separators. In preferred embodiments of the invention, separator C is a pressure swing adsorption (PSA) unit or a temperature swing adsorption (TSA) unit. In the most preferred embodiment, it is a pressure swing adsorption unit.

PSA is a well known process for separating the components of a mixture of gases by virtue of the difference in the degree of adsorption among them on a particulate adsorbent retained in a stationary bed. Typically, two or more such beds are operated in a cyclic process comprising adsorption under relatively high pressure and desorption or bed regeneration under relatively low pressure or vacuum. The strongly adsorbed component or components are adsorbed from the gas stream during the adsorption stage and desorbed from the adsorption bed during the regeneration stage. The cycle may contain other steps in addition to the fundamental steps of adsorption and regeneration, and it is commonplace to have two or more adsorbent beds cycled 180° out of phase to assure a pseudo-continuous flow of desired product. While it is conventional for the adsorption step of the PSA cycle to be carried out at superatmospheric pressure, it can run at or near atmospheric pressure, in which case the desorption will be carried out under vacuum. It is the difference in pressure between the adsorption and desorption stages which is essential for operation of the system.

When separator C is a PSA unit, the adsorbent contained therein may be any art-recognized material which adsorbs carbon dioxide to a substantially greater degree than hydrocarbons and oxygen. By proper selection of the adsorbent, the operation of the PSA unit can be readily controlled utilizing art-recognized manipulations so that the recycle stream from separator C contains a substantial portion of hydrocarbons and oxygen and a lesser percentage of carbon dioxide. Preferred adsorbents for use in separator C include carbon molecular sieves and zeolites, and carbon molecular sieves is the most preferred adsorbent.

Separator C is provided on its outlet end with waste gas discharge line 26 and hydrocarbon and oxygen recycle line 8, the latter of which, as stated above, is connected to the inlet end of reactor A. Line 8 is equipped with purge line 28.

In the process carried out in the embodiment illustrated in FIG. 1, a hydrocarbon feed stream comprising the desired hydrocarbon or hydrocarbons enters reactor A through inlet line 2 and the oxygen-containing gas stream is introduced into reactor A through line 4. In FIG. 1, the hydrocarbon feed and oxygen component are illustrated as being separately introduced into reactor A. This is a preferred arrangement since it eliminates the possibility of creating an explosive gas mixture in the feed line to reactor A. However, if desired, the hydrocarbon feed and oxygen component (and also the aqueous medium feed stream) may be combined and introduced into reactor A through a single feed line. The aqueous reaction medium, together with the fixable nitrogen compound, the hydrocarbon-utilizing microbe and any desired nutrient supplements or other additives, is introduced into reactor A through line 6.

The feed components entering reactor A intimately mix therein, assisted optionally by heating and agitating means (not shown) thereby facilitating the protein producing reaction of the invention. After a predetermined residence period the aqueous medium, which now contains the protein product, and the unreacted gases are discharged from reactor A. The aqueous medium leaving reactor A next enters protein product recovery unit B, wherein the protein is separated from the aqueous medium by conventional means and recovered as product. The aqueous medium may be recycled to aqueous medium feed line 6, or discharged from the system as spent liquid through disposal line 24.

The gaseous effluent from reactor A, which now contains, in addition to unreacted hydrocarbon and oxygen, byproduct carbon dioxide passes through line 12 and enters carbon dioxide separator C. Part or all of the carbon dioxide byproduct contained in the gaseous effluent from reactor A is separated from the hydrocarbon and oxygen mixture and discharged from the system through waste gas discharge line 26 to prevent its buildup in the system. The purified hydrocarbon and oxygen stream leaves separator C through recycle line 8 and it is recycled to reactor A. If an oxygen-rich gas other than substantially pure oxygen is used as the oxygen source, gaseous impurities, such as nitrogen and argon, will build up in the system unless these components are removed therefrom. This is accomplished by periodically or continuously purging a small amount of the hydrocarbon and oxygen recycle stream from the system through purge line 28. The purged gas mixture can be burned as fuel or otherwise disposed of.

As previously noted, there is an ever present danger of forming a flammable gas mixture in line 12 downstream of reactor A, wherein a heated mixture of hydrocarbon and oxygen exists during operation of the system. In a modified version of the invention risk of this occurrence is reduced by introducing some or all of the hydrocarbon feed requirement directly into line 12. This is accomplished by opening valve 18 and throttling down or completely closing valve 14. Hydrocarbon introduced into the system in this manner will eventually reach reactor A through recycle line 8. The high concentration of hydrocarbon in line 8 will prevent the formation of a flammable gaseous mixture in that line as well.

Figure 2:
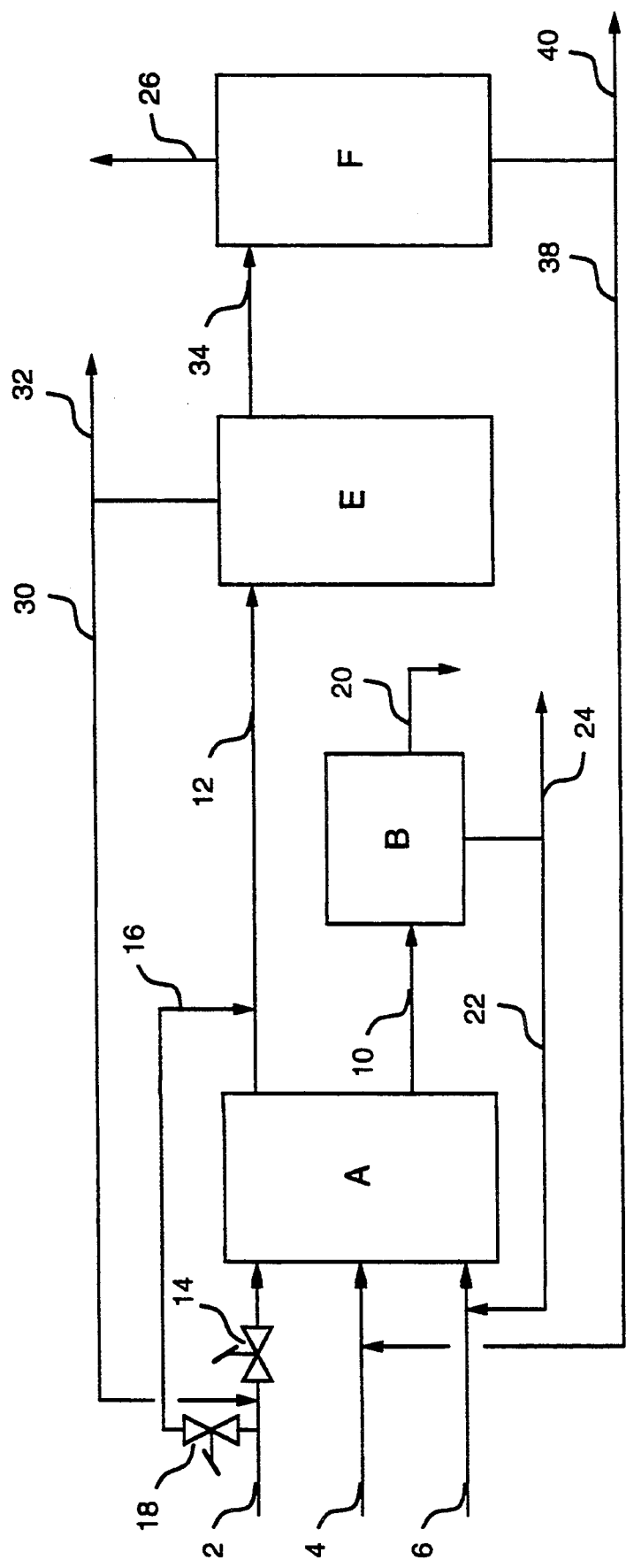
FIG. 2 illustrates in a block diagram an alternate embodiment of a system for producing proteins by the process of the invention.

The system of FIG. 2 is similar to that of FIG. 1 except that separator C of FIG. 1 is replaced by separators E and F. Separator E separates unreacted hydrocarbon from the carbon dioxide byproduct and unreacted oxygen in the gaseous effluent from reactor A, and separator F separates the unreacted oxygen from the carbon dioxide. Separator E is preferably an adsorber suitable for the separation of hydrocarbons from carbon dioxide and oxygen by pressure swing adsorption, and it may contain an adsorbent that more strongly adsorbs carbon dioxide and oxygen than hydrocarbons, but in the preferred embodiment it contains an adsorbent which more strongly adsorbs hydrocarbons than oxygen and carbon dioxide. A preferred adsorbent for this purpose is silica gel. Separator F may be identical to separator C, and in the preferred embodiment it is an adsorber containing an adsorbent suitable for the adsorption of carbon dioxide by pressure swing adsorption.

In the system illustrated in FIG. 2, separator E is provided with hydrocarbon recycle line 30 and carbon dioxide and oxygen discharge line 34. Purge line 32 is connected to line 30. Line 34 connects separator E to separator F. Separator F is also connected to carbon dioxide waste line 26 and oxygen recycle line 38. Attached to oxygen recycle line 38 is purge line 40. Hydrocarbon recycle line 30 may be connected to hydrocarbon feed line 2, as illustrated in FIG. 2, or it may be connected directly to reactor A. Similarly, oxygen recycle line 38 can be connected to oxygen component line 4, as illustrated, or it can be connected directly to reactor A.

The process practiced in the system of FIG. 2 is similar to that practiced in FIG. 1, except that the unreacted hydrocarbon and unreacted oxygen are separately recovered from the gaseous effluent from reactor A and separately recycled to reactor A. Purge line 32 may be used to remove hydrocarbons and/or impurities from the hydrocarbon recycle stream. Similarly, purge line 40 can be used to remove oxygen or impurities contained in line 38 from the system.

Figure 3:
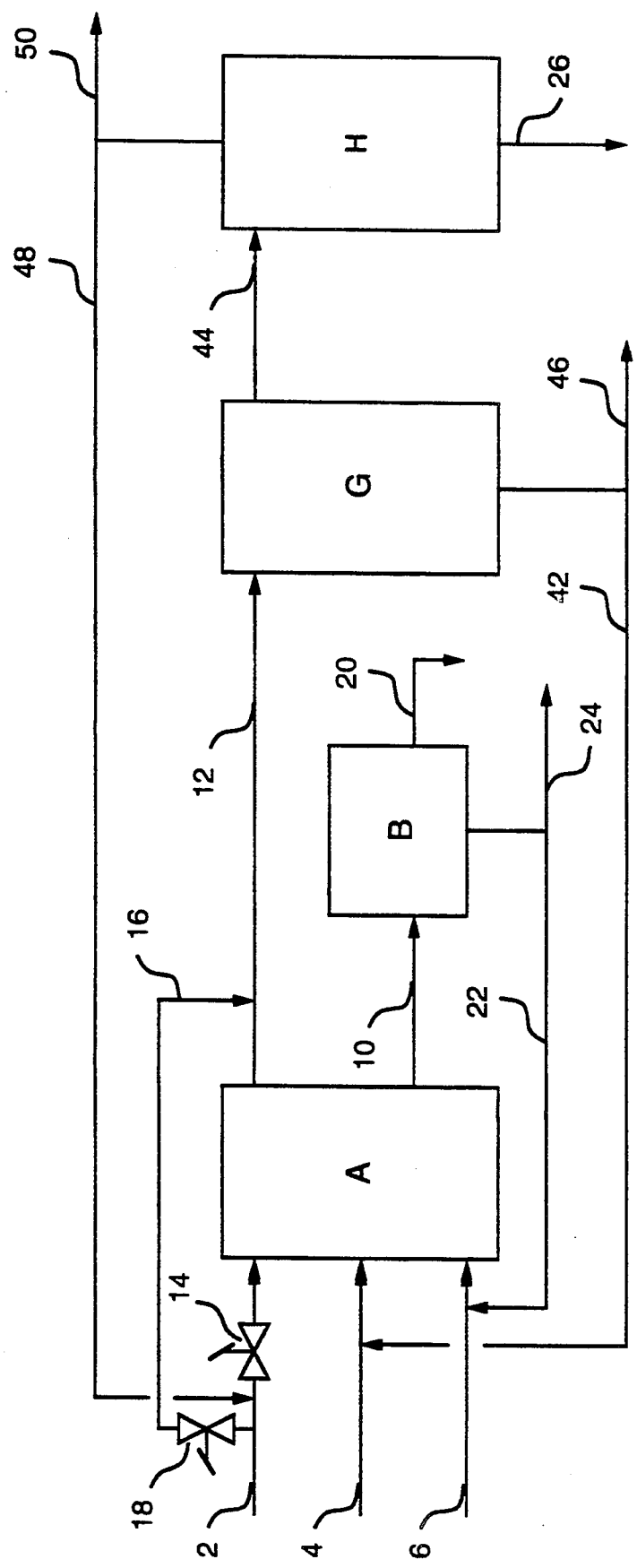
FIG. 3 illustrates in a block diagram a third embodiment of a system for producing proteins by the process of the invention.

The system of FIG. 3 is similar to that of FIG. 2 except that separators E and F of FIG. 2 are replaced by separators G and H. Separator G separates unreacted oxygen from the carbon dioxide and unreacted hydrocarbon in the gaseous effluent from reactor A, and separator H separates the unreacted hydrocarbon from the carbon dioxide. Separator G is preferably an adsorber suitable for the separation of oxygen from carbon dioxide and hydorcarbons by pressure swing adsorption, and in the preferred embodiment it generally contains an adsorbent that more strongly adsorbs carbon dioxide and hydrocarbons than oxygen. A preferred adsorbent for this purpose is activated carbon. Separator H may be identical to separator C, and in the preferred embodiment it is an adsorber containing an adsorbent which more strongly adsorbs carbon dioxide than hydrocarbons by pressure swing adsorption.

In the system illustrated in FIG. 3, separator G is provided with oxygen recycle line 42 and carbon dioxide and hydrocarbon discharge line 44. Purge line 46 is connected to line 42. Line 44 connects separator G to separator H and separator H is fitted with carbon dioxide waste line 26 and hydrocarbon recycle line 48. Attached to hydrocarbon recycle line 48 is purge line 50. Oxygen recycle line 42 may be connected to oxygen component line 4, as illustrated in FIG. 3, or it may be connected directly to reactor A. Similarly, hydrocarbon recycle line 48 may be connected to hydrocarbon feed line 2 as illustrated, or it may be connected directly to reactor A.

The process practiced in the system of FIG. 3 is similar to that practiced in FIG. 2, except that first the unreacted oxygen is recovered from the gaseous effluent from reactor A and then the unreacted hydrocarbon is recovered from this stream. As in the process practiced in the system of FIG. 2, these streams are separately recycled to reactor A. Purge line 46 may be used to remove oxygen and/or impurities from the system and purge line 50 can be used to remove unreacted hydrocarbon and/or impurities from the system.

As was the case in the process carried out in the system of FIG. 1, a stoichiometric excess of hydrocarbon can be introduced into reactor A in the processes practiced in the systems of FIGS. 2 and 3, thereby preventing the formation of a flammable mixture in reactor A or gaseous effluent line 12. Also, part or all of the hydrocarbon component introduced into the system of FIG. 3 can be introduced directly into the gaseous effluent line from reactor A. In the system of FIG. 2 however, most of the hydrocarbon introduced into separator E leaves that unit through line 30, and the low concentration of oxygen in line 30 prevents the formation of a flammable gas mixture in that line. The very high concentration of carbon dioxide in line 34 and the low concentration of hydrocarbon in oxygen recycle line 38 prevents the formation of a flammable gas mixture in those lines.

In the system of FIG. 3, most of the oxygen introduced into separator G leaves that unit through line 42. The low concentration of hydrocarbon in line 42 prevents the formation of a flammable gas mixture in that line, and the very high concentration of hydrocarbon and carbon dioxide in line 44 prevents the formation of a flammable gas mixture in line 44. The low concentration of oxygen in hydrocarbon recycle line 48 prevents the formation of a flammable gas mixture in that line.

The construction and operating details of reactor A, protein recovery unit B and separators C, E, F, G and H are all well known and form no part of the present invention.

The invention is further illustrated in the following examples, in which, unless otherwise indicated, parts, percentages and ratios are on a volume basis.

EXAMPLE I

This example is a hypothetical run based on a process carried out in the system illustrated in FIG. 1. Into a continuous loop fermentor in which an aqueous liquid maintained at a temperature of about 45° C. by cooling means is continuously circulated, are introduced oxygen, natural gas containing methane, nitrogen and carbon dioxide, various nutrient minerals and a methane-utilizing protein-synthesizing bacterium. An aqueous slurry continuously withdrawn from the reactor is subjected to centrigugal filtration to remove protein product, and the aqueous filtrate is returned to the reactor. A gas stream containing methane, oxygen, nitrogen and carbon dioxide was likewise continuously withdrawn from the reactor. A material balance of the gas stream appears in Table I.

TABLE I

| Stream | Feed | Reactor Effluent | Unit C Recycle | Waste Stream |
|---|---|---|---|---|
| $CH_4$ | 732.7 | 945.4 | 708.9 | 236.4 |
| $O_2$ | 824.1 | 319.0 | 239.2 | 79.8 |
| $N_2$ | 15.0 | 59.7 | 44.8 | 14.9 |
| $CO_2$ | 3.7 | 482.5 | 230.6 | 251.9 |
| Total | 1575.5 | 1806.5 | 1223.5 | 583.0 |

As shown in Table I, the methane and oxygen consumptions will be reduced by 49% and 22%, respectively, compared to practice of the same process but without methane and oxygen recycle. Furthermore, none of the gas streams in the system will constitute a flammable gas mixture.

EXAMPLE II

This example is a hypothetical run based on a process carried out in the system illustrated in FIG. 3. In this example the hydrocarbon stream is natural gas containing methane and nitrogen, and this stream will be introduced into reactor A gaseous effluent stream in line 12 via line 16. Also, 10% of the gaseous effluent leaving separator G through line 42 is purged from the system through line 46. A gas stream material balance appears in Table II.

TABLE II

| Stream | Feed | Reactor Effluent | Unit G Effluent | Unit G Recycle | Unit H Recycle | Waste Stream |
|---|---|---|---|---|---|---|
| $CH_4$ | 496.2 | 212.8 | 212.8 | 0.0 | 212.8 | 0.0 |
| $O_2$ | 759.2 | 186.1 | 37.2 | 134.0 | 37.2 | 0.0 |
| $N_2$ | 2.3 | 28.6 | 5.7 | 20.5 | 5.7 | 0.0 |
| $CO_2$ | 0.0 | 381.7 | 381.7 | 0.0 | 133.6 | 248.1 |
| Total | 1257.7 | 809.1 | 637.4 | 154.5 | 389.3 | 248.1 |

As shown in Table II, 212.8 moles/hr of methane and 171.2 moles/hr of oxygen are recovered in separators G and H, thereby reducing the methane and oxygen consumptions by 30% and 18.4%, respectively, compared to practice of the same process but without methane and oxygen recycle. Furthermore, none of the gas streams in the system constitutes a flammable gas mixture.

Although the invention has been described with particular reference to a specific example, it is understood that variations are contemplated. For example, the protein production reaction can be carried out under different conditions. Similarly, other adsorbents and other means of gas separation can be used in the process of the invention, if desired. Furthermore, the process of the invention can be practiced in equipment arrangements other than those illustrated in the drawings. The scope of the invention is limited only by the breadth of the appended claims.

What is claimed is:

1. In a process for producing a protein comprising contacting a hydrocarbon feed stream comprising at least one gaseous hydrocarbon and an oxygen-rich gas in an aqueous medium in a reaction zone in the presence of a microbe capable of converting said gaseous hydrocarbons to protein, thereby producing an aqueous phase containing said protein and a gaseous phase containing unreacted gaseous hydrocarbon, unreacted oxygen and carbon dioxide, said gaseous phase containing sufficient gaseous hydrocarbon to render it nonflammable; and removing protein from said reaction zone; the improvement comprising passing said gaseous phase through a carbon dioxide separator, thereby separating carbon dioxide from said gaseous phase; and recycling at least part of the carbon dioxide:depleted gaseous phase to said reaction zone.

2. The process of claim 1, wherein gaseous hydrocarbon is introduced into the gaseous effluent from said reaction zone.

3. The process of claim 2, wherein the gaseous hydrocarbon introduced into the gaseous effluent comprises at least part of the gaseous hydrocarbon entering said system.

4. The process of claim 1 or claim 2, wherein said carbon dioxide separator is a pressure swing adsorption system containing an adsorbent which more strongly adsorbs carbon dioxide than oxygen and gaseous hydrocarbons.

5. The process of claim 4, wherein said hydrocarbon stream is selected from natural gas and substantially pure methane and said oxygen-rich gas is substantially pure oxygen.

6. In a process for producing a protein comprising the steps of contacting at least one gaseous hydrocarbon and an oxygen-rich gas in an aqueous medium in a reaction zone in the presence of a microbe capable of converting said at least one gaseous hydrocarbon to protein, thereby producing an aqueous phase containing protein and a gaseous phase containing unreacted gaseous hydrocarbon, unreacted oxygen and carbon dioxide, said gaseous phase containing sufficient gaseous hydrocarbon to render it nonflammable; and removing protein from said reaction zone; the improvement comprising:

(a) passing said gaseous phase through a pressure swing adsorption zone which contains an adsorbent which more strongly adsorbs hydrocarbons than carbon dioxide and oxygen, thereby producing a gaseous hydrocarbon-rich stream and a gas stream rich in oxygen and carbon dioxide;

(b) passing said gas stream rich in oxygen and carbon dioxide through a carbon dioxide separator, thereby producing a carbon dioxide-rich stream and an oxygen-rich stream; and (c) recycling at least part of said gaseous hydrocarbon-rich stream and at least part of said oxygen-rich stream to said reaction zone.

7. The process of claim 6, wherein gaseous hydrocarbon is introduced into the gaseous effluent from said reaction zone.

8. The process of claim 7, wherein the gaseous hydrocarbon introduced into the gaseous effluent comprises at least part of the gaseous hydrocarbon entering said system.

9. The process of claim 6 or claim 7, wherein said carbon dioxide separator is a pressure swing adsorption system containing an adsorbent which more strongly adsorbs carbon dioxide than oxygen.

10. The process of claim 9, wherein said hydrocarbon stream is selected from natural gas and substantially pure methane and said oxygen-rich gas is substantially pure oxygen.

11. In a process for producing a protein comprising the steps of contacting at least one gaseous hydrocarbon and an oxygen-rich gas in an aqueous medium in a reaction zone in the presence of microbe capable of converting said gaseous hydrocarbons to protein, thereby producing an aqueous phase containing protein and a gaseous phase containing unreacted gaseous hydrocarbon, unreacted oxygen and carbon dioxide, said gaseous phase containing sufficient gaseous hydrocarbon to render it nonflammable; and removing protein from said reaction zone; the improvement comprising:

(a) passing said gaseous phase through a pressure swing adsorption zone which contains an adsorbent which more strongly adsorbs carbon dioxide and gaseous hydrocarbons than oxygen, thereby producing an oxygen-rich stream and a stream rich in gaseous hydrocarbons and carbon dioxide;

(b) passing said gas stream rich in gaseous hydrocarbons and carbon dioxide through a carbon dioxide separator, thereby producing a carbon dioxide-rich stream and a gaseous hydrocarbon-rich gas stream; and (c) recycling at least part of said oxygen-rich stream and at least part of said gaseous hydrocarbon-rich stream to said reaction zone.

12. The process of claim 11, wherein gaseous hydrocarbon is introduced into the gaseous effluent from said reaction zone.

13. The process of claim 12, wherein the gaseous hydrocarbon introduced into the gaseous effluent comprises at least part of the gaseous hydrocarbon entering said system.

14. The process of claim 11 or claim 12, wherein said carbon dioxide separator is a pressure swing adsorption system containing an adsorbent which more strongly adsorbs carbon dioxide than gaseous hydrocarbons.

15. The process of claim 14, wherein said hydrocarbon stream is selected from natural gas and substantially pure methane and said oxygen-rich gas is substantially pure oxygen.

16. The process of any one of claims 1, 2, 6, 7, 11 or 12, wherein said at least one gaseous hydrocarbon is selected from hydrocarbons having 1 to 4 carbon atoms.

17. The process of any one of claims 1, 2, 6, 7, 11 or 12, wherein said oxygen-rich gas is substantially pure oxygen or oxygen-enriched air.

18. The process of claim 17, wherein said at least one gaseous hydrocarbon is natural gas or methane.

* * * * *